United States Patent [19]

Goodin

[11] Patent Number: 5,425,712
[45] Date of Patent: Jun. 20, 1995

[54] DILATATION CATHETER HAVING SOFT BUMPER TIP

[75] Inventor: Richard L. Goodin, Blaine, Minn.

[73] Assignee: Schneider (USA) Inc., Plymouth, Minn.

[21] Appl. No.: 287,062

[22] Filed: Aug. 8, 1994

Related U.S. Application Data

[63] Continuation of Ser. No. 45,953, Apr. 9, 1993, abandoned.

[51] Int. Cl.⁶ .................... A61M 25/00; A61M 29/00
[52] U.S. Cl. ........................................ 604/96; 606/192
[58] Field of Search ................... 604/96–103; 606/192–196; 600/18

[56] References Cited

U.S. PATENT DOCUMENTS

| | | |
|---|---|---|
| 3,769,117 | 10/1973 | Bowen . |
| 4,323,071 | 4/1982 | Simpson et al. . |
| 4,464,176 | 8/1984 | Wijayarathna . |
| 4,496,345 | 1/1985 | Hasson . |
| 4,597,755 | 7/1986 | Samson et al. . |
| 4,739,768 | 4/1988 | Engelson . |
| 4,892,519 | 1/1990 | Songer et al. . |
| 4,921,483 | 5/1990 | Wijay et al. . |
| 4,955,895 | 9/1990 | Sugiyama et al. . |
| 4,960,410 | 10/1990 | Pinchuk . |
| 4,976,690 | 12/1990 | Solar et al. . |
| 5,047,045 | 9/1991 | Arney et al. ................... 606/194 |
| 5,098,381 | 3/1992 | Schneider ....................... 604/96 |
| 5,100,381 | 3/1992 | Burns . |
| 5,100,385 | 3/1992 | Bromander ..................... 604/99 |
| 5,176,637 | 1/1993 | Sagae . |
| 5,217,434 | 6/1993 | Arney ............................. 604/99 |
| 5,221,260 | 6/1993 | Burns et al. .................... 604/99 |

FOREIGN PATENT DOCUMENTS

| | | |
|---|---|---|
| 131918A3 | 1/1985 | European Pat. Off. . |
| 334640A2 | 9/1989 | . |
| 0405831A2 | 1/1991 | European Pat. Off. . |
| 408198A1 | 1/1991 | European Pat. Off. . |
| 437121A3 | 7/1991 | European Pat. Off. . |
| 512359A1 | 11/1992 | European Pat. Off. . |
| 0513818A1 | 11/1992 | European Pat. Off. . |
| 2550454 | 11/1983 | France . |

OTHER PUBLICATIONS

*Hytrel polyester elastomer, General Guide to Products & Properties,* Dupont, Sep. 1984.

Notification of Transmittal of International Search Report, International Search Report and one-page annex in PCT/US 94/01908.

Primary Examiner—C. Fred Rosenbaum
Assistant Examiner—Adam J. Cermak
Attorney, Agent, or Firm—Peter C. Richardson; Lawrence C. Akers; Philip C. Strassburger

[57] ABSTRACT

A balloon dilatation catheter is disclosed having a multisectioned inner tube having a soft bumper tip, a multisectioned outer tube and a balloon with its distal neck connected to the bumper tip and its proximal neck connected to the outer tube. The various sections of the inner tube and outer tube may be formed from different materials or different grades of the same material. In addition, each section may have different outer diameters. The outer tube is bonded directly to the inner tube at the distal end of the outer tube. Preferably this bond is accomplished by thermal bonding.

14 Claims, 2 Drawing Sheets

DILATATION CATHETER HAVING SOFT BUMPER TIP

This is a continuation, of application Ser. No. 08/045,953, filed on Apr. 9, 1993 now abandoned.

BACKGROUND OF THE INVENTION

This invention relates to vascular catheters for use in percutaneous transluminal angioplasty procedures. In particular, this invention relates to a balloon dilatation catheter for use in percutaneous transluminal coronary angioplasty.

In percutaneous transluminal coronary angioplasty, a guidewire is introduced into a patient's vascular system usually in the femoral artery and advanced to the site of a stenosis in one of the coronary arteries. A balloon dilatation catheter having a balloon at its distal end is then advanced over the guidewire until the balloon is positioned at the stenosis site. The balloon on the catheter is then inflated to exert compression forces against the stenosis. In this manner, the artery can be dilated so a more adequate flow of blood therethrough can be established.

A typical over the wire balloon dilatation catheter comprises an outer tube, an inner tube disposed within the outer tube and extending beyond the distal end of the outer tube and a balloon mounted adjacent to the distal end of the catheter. The proximal neck of the balloon is connected to the outer tube while the distal neck of the balloon is connected to the inner tube. The inner tube defines the guidewire lumen. The annular space between the inner tube and the outer tube defines the inflation lumen and is in communication with the balloon cavity.

In coronary applications, such a balloon dilatation catheter must be pushed a long distance from the body access site to the treatment site. In addition, the catheter must be maneuvered through numerous arterial branches to get to the particular coronary blood vessel where treatment is desired. This requires the balloon dilatation catheter to follow a convoluted and tortuous path. Thus the balloon dilatation catheter must be stiff enough along its proximal portion to allow the catheter to be advanced to the treatment site and yet be flexible enough along its distal portion to follow such a tortuous path. The balloon dilatation catheter must also have a low profile to allow it to be advanced through small coronary arteries and yet have an inflation lumen sufficiently large to allow the balloon to be inflated and deflated quickly.

It would therefore be desirable to provide a balloon dilatation catheter that is flexible enough to negotiate a convoluted and tortuous path through the vascular system yet be stiff enough so it can be pushed through the vascular system.

It would also be desirable to provide a balloon dilatation catheter that has a low profile yet has an inflation lumen that is sufficiently large to allow the balloon to be inflated and deflated quickly.

SUMMARY OF THE INVENTION

These and other objects and advantages are achieved by the balloon dilatation catheter of the present invention. This catheter comprises an inner catheter having a first lumen extending therethrough, an outer catheter having a second lumen extending therethrough and a balloon. The inner catheter is disposed in the second lumen of the outer catheter so that a predetermined length of the distal portion of the inner catheter extends beyond the distal end of the outer catheter. The inner catheter and the outer catheter are each formed from multiple tubes.

The inner catheter is formed from a proximal inner tube, a distal inner tube and a bumper tip. The outer diameter of the proximal inner tube is greater than the outer diameter of the distal inner tube. However, the wall thicknesses are the same in the proximal inner tube and the distal inner tube. The outer catheter is formed from a proximal outer tube and a distal stem. In addition, the outer diameter of the proximal outer tube is greater than the outer diameter of the distal stem. However, the wall thickness in the distal stem is at least as large as the wall thickness in the proximal outer tube.

The first lumen defines the guidewire lumen. A space is formed between the inner surface of the outer catheter and the outer surface of the inner catheter. This space defines the inflation lumen. The balloon has an internal balloon cavity that communicates with the inflation lumen. The proximal neck portion of the balloon is bonded to the distal stem while the distal neck portion of the balloon is bonded to the bumper tip. The juncture between the distal inner tube and the bumper tip is located inside of the balloon cavity. The distal stem is bonded directly to the distal inner tube adjacent to the proximal neck portion of the balloon at the distal end of the distal stem.

BRIEF DESCRIPTION OF THE DRAWINGS

The above and other objects and advantages of this invention will be apparent upon consideration of the following detailed description, taken in conjunction with the accompanying drawings, in which like reference characters refer to like parts throughout and in which.

DETAILED DESCRIPTION OF THE INVENTION

Figure 1:
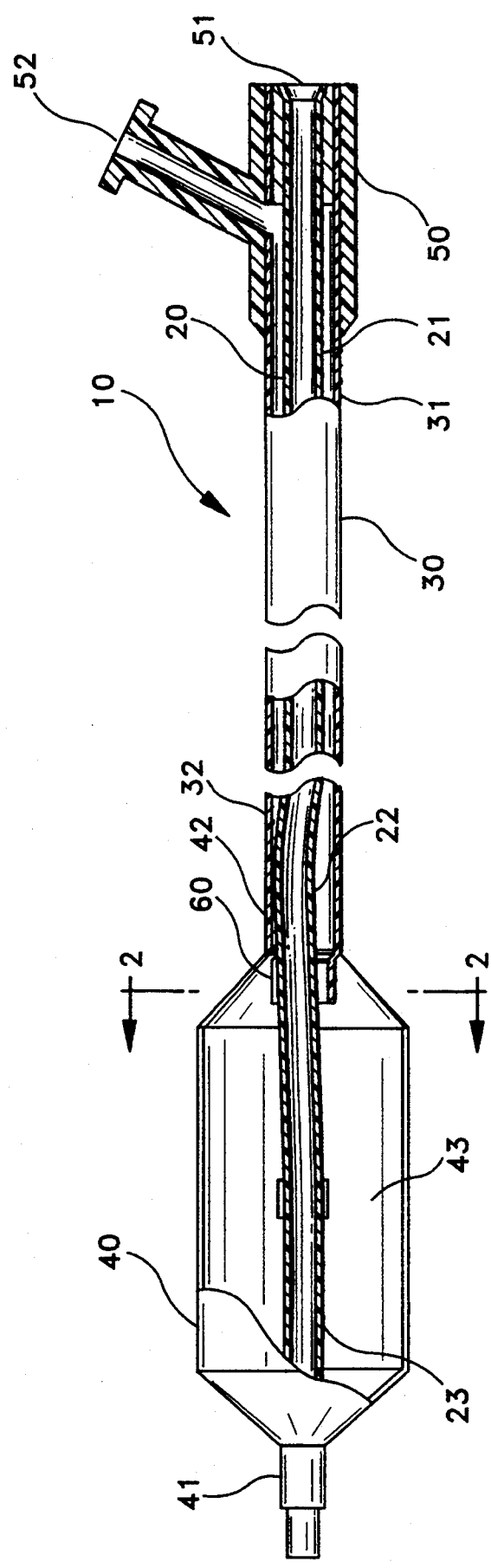
FIG. 1 is a partial sectional view of the balloon dilatation catheter of the present invention.

The balloon dilatation catheter 10 of the present invention has an inner catheter 20, an outer catheter 30 and a balloon 40. Inner catheter 20 comprises a proximal inner tube 21, a distal inner tube 22 and a bumper tip 23. These three elements define a guidewire lumen extending therethrough. Outer catheter 30 comprises a proximal outer tube 31 and a distal stem 32. These two elements define a second lumen extending therethrough. Inner catheter 20 is disposed inside the second lumen of outer catheter 30 so that a predetermined length of the distal portion of inner catheter 20 extends out of the distal end of outer catheter 30. An unoccluded space still remains in the second lumen between the inner surface of outer catheter 30 and the outer surface of inner catheter 20 when inner catheter 20 is inserted into the second lumen to define an inflation lumen.

Balloon 40 is disposed about inner catheter 20 and has its distal neck 41 connected to bumper tip 23 and its proximal neck 42 connected to distal stem 32. The bond between distal neck 41 and bumper tip 23 and the bond between proximal neck 42 and distal stem 32 can be achieved by the application of heat. Preferably a laser bond, such as described in copending application Ser.

No. 07/800,201 filed Nov. 29, 1991 is used. The balloon cavity 43 is in communication with the inflation lumen. Balloon 40 can be formed from a variety of materials such as polyethylene, polyethylene terephthalate or nylon.

The proximal ends of proximal outer tube 31 and proximal inner tube 21 are inserted into and held securely by a branched hub 50. A first opening 51 and a second opening 52 are formed in branched hub 50. First opening 51 is in communication with the guidewire lumen of inner catheter 20. This arrangement allows a guidewire (not shown) to extend inside inner catheter 20 from the proximal end of catheter 10 and out past the distal end of catheter 10. Second opening 52 is in communication with the inflation lumen. This arrangement allows inflation fluid to be injected in second opening 52 through the inflation lumen and into balloon cavity 43 to thereby inflate balloon 40.

The material used to form the various elements of inner catheter 20 and outer catheter 30 should be selected to give catheter 10 sufficient pushability at its proximal portion and sufficient flexibility at its distal portion.

For example, a relatively stiff material should be selected for proximal outer tube 31 and proximal inner tube 21 while a relatively flexible material should be selected for distal stem 32, distal inner tube 22 and bumper tip 23. It has been found that enhanced performance, measured by the pushability of catheter 10 through the vascular system and the trackability of catheter 10 over a guidewire through tortuous coronary arteries, is achieved by the use of polyethylene for proximal inner tube 21 and various grades of polyester for the remaining elements of inner catheter 20 and outer catheter 30. Preferably DuPont HYTREL polyester is used. Proximal outer tube 31 is 72 D, distal stem 32 is 55 D, distal inner tube 22 is 63 D and bumper tip 23 is 45 D. When bumper tip 23 is made from such a soft material as 45 D Hytrel® polyester, trauma to the blood vessel in which catheter 10 is inserted is minimized as catheter 10 tracks a guidewire to a treatment site.

The relative dimensions of the various elements forming inner catheter 20 and outer catheter 30 are also selected to give enhanced performance. For example, the outer diameter of proximal outer tube 31 is larger than the outer diameter of distal stem 32. This provides outer catheter 30 with a relatively stiff proximal portion having decreasing stiffness toward the distal portion. The wall thickness of distal stem 32 is at least as large as the wall thickness of proximal outer tube 31. In addition, the outer diameter of proximal inner tube 21 is larger than the outer diameter of distal inner tube 22. Preferably the wall thickness of proximal inner tube 21 should be equal to or smaller than the wall thickness of distal inner tube 22. Preferably the outer diameter and wall thickness of bumper tip 23 are larger than the outer diameter and wall thickness of proximal inner tube 21. This arrangement yields inner catheter 20 with increasing flexibility from the proximal portion to the distal portion. In addition, the relative wall thicknesses prevent the guidewire lumen located inside balloon cavity 43 from collapsing when balloon 40 is inflated.

The various elements of inner catheter 20 and outer catheter 30 are bonded end to end by thermal bonding, laser bonding, adhesive bonding or by conventional mechanical means. The distal end of proximal inner tube 21 is bonded to the proximal end of distal inner tube 22 by heat, laser bonding, chemical adhesive or other conventional mechanical means. Similarly, the distal end of distal inner tube 22 is bonded to the proximal end of bumper tip 23 by heat, laser bonding, chemical adhesive or other conventional mechanical means. The distal end of proximal outer tube 31 is bonded to the proximal end of distal stem 32 by heat, laser bonding, chemical adhesive or other conventional mechanical means. Preferably distal neck 41 is bonded to bumper tip 23 at about the midpoint of bumper tip 23 so that the juncture between bumper tip 23 and distal inner tube 22 is located inside of balloon cavity 43.

Distal stem 32 is preferably bonded to distal inner tube 22 adjacent to proximal neck 42 of balloon 40. Any type of bond can be used. For example, distal stem 32 can be bonded to distal inner tube 22 by a chemical adhesive, a thermal bond, laser bonding or by any conventional mechanical bonding means. Preferably a thermal bond is used.

In one method of thermally bonding distal stem 32 to distal inner tube 22, a first mandrel is placed inside the lumen of distal inner tube 22 and another crescent shaped mandrel is placed inside the lumen of distal stem 32 along one portion of the outside of distal inner tube 22. The first mandrel maintains the patency of the lumen of distal inner tube 22 during the thermal bonding procedure. The crescent shaped mandrel is used to maintain the patency of the lumen of distal stem 32 between the outer surface of distal inner tube 22 and the inner surface of distal stem 32. In addition, this crescent shaped mandrel positions a portion of distal inner tube 22 into contact with distal stem 32.

A heat shrink tube is placed over distal stem 32 in the area where the bond 60 is to occur prior to the application of heat. A double jaw clamp is then positioned over the heat shrink tube. One jaw is heated while the other jaw is cooled. The heated jaw contacts the heat shrink tube in the area where distal inner tube 22 contacts distal stem 32 to bond them together. The cooled jaw contacts the remaining portion of the heat shrink tube. The amount of heat applied, i.e. time and temperature, depends on the material used for distal inner tube 22 and distal stem 32 and can be determined by simple, routine experimentation. Since it is preferable that distal inner tube 22 and distal stem 32 are formed from different grades of the same material, a homogeneous bond occurs between distal inner tube 22 and distal stem 32. After sufficient heat is applied to weld a portion of distal inner tube 22 to a portion of distal stem 32, the heat shrink tube is removed leaving distal stem 32 bonded to distal inner tube 22 at bond 60.

Figure 2:
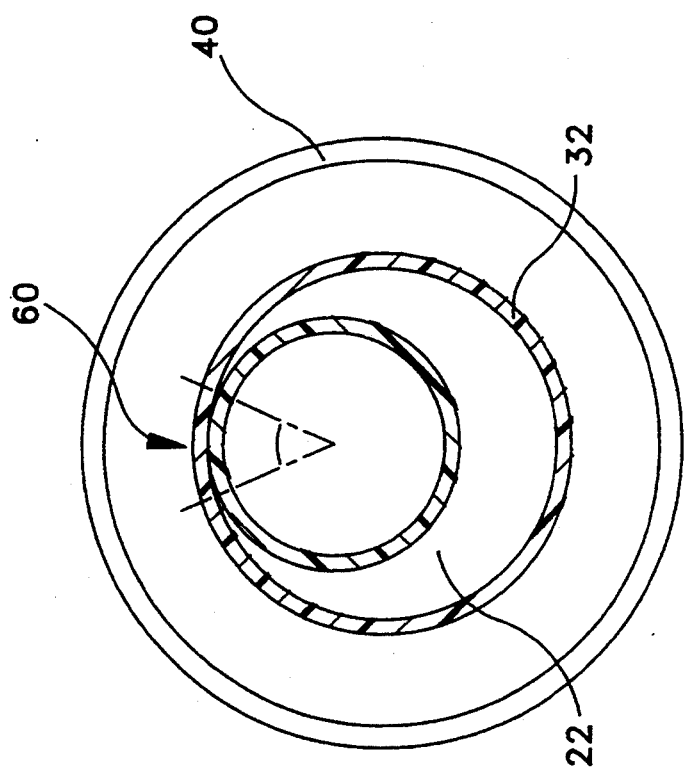
FIG. 2 is a schematic sectional view taken along line 2—2 of FIG. 1.

Bond 60 should extend along distal inner tube 22 and distal stem 32 a distance sufficient to ensure a secure bond. Bond 60 extends from the most distal end of distal stem 32 proximally for at least 0.030 inches. Preferably bond 60 extends about 0.25 inches. In addition, bond 60 should extend around distal stem 32 for a distance sufficient to ensure a secure bond. See FIG. 2. Preferably bond 60 extends from about 10° to about 350° around distal stem 32. The exact bond angle depends on the size of distal inner tube 22 and distal stem 32 and the desired minimum unoccluded space for the inflation lumen. Preferably, bond 60 extends around distal stem 32 about 30° to about 90°. This leaves sufficient space in the inflation lumen for inflation fluid to pass therethrough and rapidly inflate and deflate balloon 40. The exact combination of bond angle and bond length should be chosen to maximize the suppleness of bond 60 and maximize the unoccluded space of inflation lumen past bond 60.

Although distal stem 32 and bond 60 are shown extending into balloon cavity 43, it is also possible for distal stem 32 to terminate at its distal end at proximal neck 42 of balloon 40 so that bond 60 occurs at proximal neck 42. However, it is preferable that the distal end of distal stem 32, along with bond 60, extend into balloon cavity 43. This arrangement minimizes the material bonded at one point and thus maximizes the trackability of catheter 10 along a guidewire.

Thus, it is seen that a balloon dilatation catheter is provided that is flexible enough to negotiate a convoluted and tortuous path through the vascular system yet is stiff enough to be pushed through the vascular system and has a low profile yet has a inflation lumen that minimizes balloon inflation and deflation times. One skilled in the art will appreciate that the described embodiments are presented for purposes of illustration and not of limitation and that the present invention is only limited by the claims which follow.

I claim:

1. A catheter comprising:
an inner tube having a proximal inner tube with a distal end, a distal inner tube with a distal end and a proximal end and a bumper tip with a proximal end, the proximal end of the distal inner tube being bonded to the distal end of the proximal inner tube and the proximal end of the bumper tip being bonded to the distal end of the distal inner tube to define a bumper tip bonding juncture and a first lumen extending through the proximal inner tube, the distal inner tube and the bumper tip to define a guidewire lumen, the bumper tip being formed from a material that is softer than the material used to form the distal inner tube, the bumper tip material having a hardness of less than 63 D;
an outer tube having a proximal outer tube with a distal end and a distal stem with a distal end and a proximal end, the proximal end of the distal stem bonded to the distal end of the proximal outer tube and a second lumen extending through the proximal outer tube and the distal stem;
the inner tube being disposed in the outer tube so that a predetermined length of the distal inner tube and bumper tip extends beyond the distal end of the distal stem with an unoccluded space remaining between an inner surface of the outer tube and an outer surface of the inner tube to define an inflation lumen; and
a balloon defining a balloon cavity in communication with the inflation lumen and having a proximal neck bonded to the distal stem and a distal neck bonded to the bumper tip adjacent to a medial portion of the bumper tip so that the bumper tip bonding juncture is located inside the balloon cavity.

2. The catheter of claim 1 wherein the proximal outer tube has an outer diameter larger than the outer diameter of the distal stem.

3. The catheter of claim 2 wherein the proximal inner tube has an outer diameter that is larger than the outer diameter of the distal inner tube.

4. The catheter of claim 3 wherein the proximal inner tube is formed from polyethylene.

5. The catheter of claim 2 wherein the proximal inner tube is formed from polyethylene.

6. The catheter of claim 1 wherein the proximal inner tube has an outer diameter that is larger than the outer diameter of the distal inner tube.

7. The catheter of claim 6 wherein the proximal inner tube is formed from polyethylene.

8. The catheter of claim 1 wherein the proximal inner tube is formed from polyethylene.

9. The catheter of claim 1 wherein the proximal outer tube, the distal stem, the distal inner tube and the bumper tip are all formed from different grades of polyester.

10. The catheter of claim 1 wherein the catheter is configured to provide sufficient flexibility to negotiate the vascular system and is further configured to provide sufficient stiffness so it can be pushed through the vascular system.

11. The catheter of claim 1 wherein the bumper tip material has a hardness of about 45 D.

12. The catheter of claim 1 wherein the distal inner tube material has a hardness of about 63 D.

13. The catheter of claim 1 wherein the hardness of the distal inner tube and the hardness of the bumper tip is in a ratio of about 1.4.

14. A catheter comprising:
an inner tube having a proximal inner tube with a distal end, a distal inner tube with a distal end and a proximal end and a bumper tip with a proximal end, the proximal end of the distal inner tube being bonded to the distal end of the proximal inner tube and the proximal end of the bumper tip being bonded to the distal end of the distal inner tube to define a bumper tip bonding juncture and a first lumen extending through the proximal inner tube, the distal inner tube and the bumper tip to define a guidewire lumen, the bumper tip being formed from a material that is softer than the material used to form the distal inner tube;
an outer tube having a proximal outer tube with a distal end and a distal stem with a distal end and a proximal end, the proximal end of the distal stem bonded to the distal end of the proximal outer tube and a second lumen extending through the proximal outer tube and the distal stem;
the inner tube being disposed in the outer tube so that a predetermined length of the distal inner tube and bumper tip extends beyond the distal end of the distal stem with an unoccluded space remaining between an inner surface of the outer tube and an outer surface of the inner tube to define an inflation lumen; and
a balloon defining a balloon cavity in communication with the inflation lumen and having a proximal neck bonded to the distal stem and a distal neck bonded to the bumper tip adjacent to a medial portion of the bumper tip so that the bumper tip bonding juncture is located inside the balloon cavity.

* * * * *